(12) United States Patent
Rogers, Jr.

(10) Patent No.: US 9,757,531 B2
(45) Date of Patent: *Sep. 12, 2017

(54) TRANSPORTABLE MEDICAL AIR COMPRESSOR

(71) Applicant: Draeger Medical Systems, Inc., Telford, PA (US)

(72) Inventor: David Duane Rogers, Jr., Quakertown, PA (US)

(73) Assignee: Draeger Medical Systems, Inc., Telford, PA (US)

( * ) Notice: Subject to any disclaimer, the term of this patent is extended or adjusted under 35 U.S.C. 154(b) by 526 days.

This patent is subject to a terminal disclaimer.

(21) Appl. No.: 14/310,436

(22) Filed: Jun. 20, 2014

(65) Prior Publication Data
US 2014/0301871 A1 Oct. 9, 2014

Related U.S. Application Data

(62) Division of application No. 13/697,215, filed as application No. PCT/US2011/059180 on Nov. 3, 2011, now Pat. No. 8,821,133.

(51) Int. Cl.
| A61M 16/10 | (2006.01) |
| A61M 16/22 | (2006.01) |
| A61M 16/00 | (2006.01) |

(52) U.S. Cl.
CPC ...... A61M 16/0063 (2014.02); A61M 16/107 (2014.02); A61M 16/1055 (2013.01);
(Continued)

(58) Field of Classification Search
CPC .. A61G 10/04; A61G 11/009; A61G 2203/46; A61M 16/00; A61M 16/0045; A61M 16/0051; A61M 16/0057; A61M 16/0063; A61M 16/0069; A61M 16/0808; A61M 16/0858; A61M 16/10; A61M 16/1055; A61M 16/1075; A61M 16/145; A61M 16/16; A61M 16/20; A61M 16/22; A61M 2016/0024; A61M 2016/0027; A61M 2202/0233; A61M 2205/0205;
(Continued)

(56) References Cited

U.S. PATENT DOCUMENTS

| 4,342,573 A | 8/1982 | McCombs et al. |
| 4,505,128 A | 3/1985 | Miller et al. |
(Continued)

FOREIGN PATENT DOCUMENTS

| CN | 2241550 | 12/1996 |
| WO | WO00/54854 | 9/2000 |

OTHER PUBLICATIONS

Praxair Healthcare Services. "Medical Gases and Equipment Catalog". 2010.*
(Continued)

*Primary Examiner* — Annette Dixon
(74) *Attorney, Agent, or Firm* — DLA Piper LLP (US)

(57) ABSTRACT

A method and apparatus that provides a continuous source of medical grade air. A substantially tubular housing includes a first end, an aperture extending through the housing, and a second end, opposite the first end. A valve extends from the first end of the housing for dispensing medical grade air to a patient.

7 Claims, 11 Drawing Sheets

(52) U.S. Cl.
CPC ..... *A61M 16/22* (2013.01); *A61M 2016/0027* (2013.01); *A61M 2205/3368* (2013.01)

(58) Field of Classification Search
CPC .. A61M 2205/3331; A61M 2205/3368; A61M 2205/3606; A61M 2205/362; A61M 2205/583; A61M 2205/7509; A61M 2205/7518; A61M 2205/7545; A61M 2205/8206; A61M 2230/205; A63B 2213/006; A63B 23/18
USPC ............ 128/204.15, 204.18, 204.21, 204.23, 128/205.23, 205.24
See application file for complete search history.

(56) References Cited

U.S. PATENT DOCUMENTS

| | | |
|---|---|---|
| 4,511,377 A | 4/1985 | McCombs |
| 4,576,616 A | 3/1986 | Mottram et al. |
| 4,826,510 A | 5/1989 | McCombs |
| 4,971,609 A | 11/1990 | Pawlos |
| 4,983,190 A | 1/1991 | Verrando et al. |
| 5,144,945 A | 9/1992 | Nishino et al. |
| 6,220,245 B1 | 4/2001 | Takabayashi et al. |
| 6,805,122 B2 | 10/2004 | Richey et al. |
| 7,156,903 B2 | 1/2007 | McCombs |
| 7,179,326 B2 | 2/2007 | Nakamura et al. |
| 2002/0014237 A1* | 2/2002 | Richey, II ............. A61M 16/10 128/203.25 |
| 2005/0139214 A1 | 6/2005 | Yagi et al. |
| 2009/0178675 A1* | 7/2009 | Turiello ................. A62B 13/00 128/202.13 |

OTHER PUBLICATIONS

BOC Healthcare. "Medical gas cylinder data chart". 2009.*
Chinese Office Action from corresponding CN Application No. 201180028864.9 dated Jul. 3, 2015.
First Office Action dated May 3, 2017, of corresponding Chinese Application No. 201510862682.1, along with an English translation.

* cited by examiner

TRANSPORTABLE MEDICAL AIR COMPRESSOR

FIELD OF THE INVENTION

The present invention relates to a medical air compression system, and specifically, to a portable medical air compressor designed to provide a continuous source of transportable breathing air.

BACKGROUND OF THE INVENTION

Medical grade air is a pharmaceutical product commonly used in breathing applications and used for the calibration of respiratory medical equipment. Standards for medical grade air are governed by the National Fire Protection Agency (NFPA) under the United States Pharmacopeia (USP). The USP standard requires medical air to contain between 19.5% and 23.5% oxygen, with the predominant balance being nitrogen. The USP also requires medical air to have a carbon monoxide level of less than 10 ppm, a carbon dioxide level of less than 500 ppm, a nitrogen dioxide level of less than 2.5 ppm, a nitric oxide level of less than 2.5 ppm and a sulfur dioxide level of less than 5 ppm. In addition, NFPA indicates acceptable levels of moisture and pollutants in the medical grade air such that the medical grade air contains less than 5 mg/m$^3$ of permanent particulates sized 1 micron or larger at normal atmospheric pressure.

Presently, medical air may be transported and delivered in various ways. Medical air may be transported and delivered to a patient via a medical air cylinder. These cylinders are able to store a predetermined amount of medical grade air in a reservoir contained therein. These cylinders have a finite amount of air stored therein and, upon depletion thereof, must be replaced with a new cylinder and subsequently refilled prior to their next use. Additionally, transport of these cylinders is affected by weight, size, and shape thereof which may limit the usability of these cylinders in a medical transport scenario. A drawback associated with this manner of providing medical grade air is their finite storage and the difficulty level associated with refilling the cylinders for repeated use. It is also known to provide medical grade air using a medical grade air compressor. However, currently available medical grade air compression systems are in a box or suitcase. They are typically carried to ambulances or other emergency vehicles. In addition, some current systems have to be hooked up to a medical grade air line.

Therefore a need exists to provide a continuous supply of medical grade air that does not require connection to a medical grade air line and which is conveniently transportable in vehicles and throughout a healthcare enterprise. An apparatus according to invention principles addresses deficiencies of known systems and improves patient access to a medical grade air supply.

SUMMARY OF THE INVENTION

In one embodiment, an apparatus that provides a continuous source of medical grade air is provided. A substantially tubular and rigid housing includes a first end, at least one aperture extending through the housing and positioned a predetermined distance from the first end; and a second end, opposite the first end. A valve extends from the first end of the housing for dispensing medical grade air to a patient. A medical grade air compressor provides medical grade air for output by the valve, the medical grade air compressor being positioned within the housing on a side of the at least one aperture opposite the valve. An air flow generator is positioned between the second end of the housing and the medical grade air compressor, the air flow generator draws air into the housing through the at least one aperture. The air passes over and around the medical grade air compressor to reduce a temperature of the medical grade air compressor and to the medical grade air compressor for generating medical grade air.

In another embodiment, a reservoir is positioned between the valve and the medical grade air compressor for storing compressed medical grade air generated by the medical grade air compressor and a plurality of apertures positioned around a circumference of the housing.

A further embodiment including a method of providing a continuous supply of medical grade air is provided. The method includes the activities of drawing air into a housing via at least one aperture in the housing using the air flow generator, causing the air to flow over and around a medical grade air compressor to reduce a temperature of the medical grade air compressor and receiving the air at an intake port of the medical grade air compressor for conditioning and compression thereof to generate medical grade air, and outputting the compressed and conditioned medical grade air via a valve.

BRIEF DESCRIPTION OF THE DRAWING FIGURES

DETAILED DESCRIPTION OF THE INVENTION

Figure 1A:
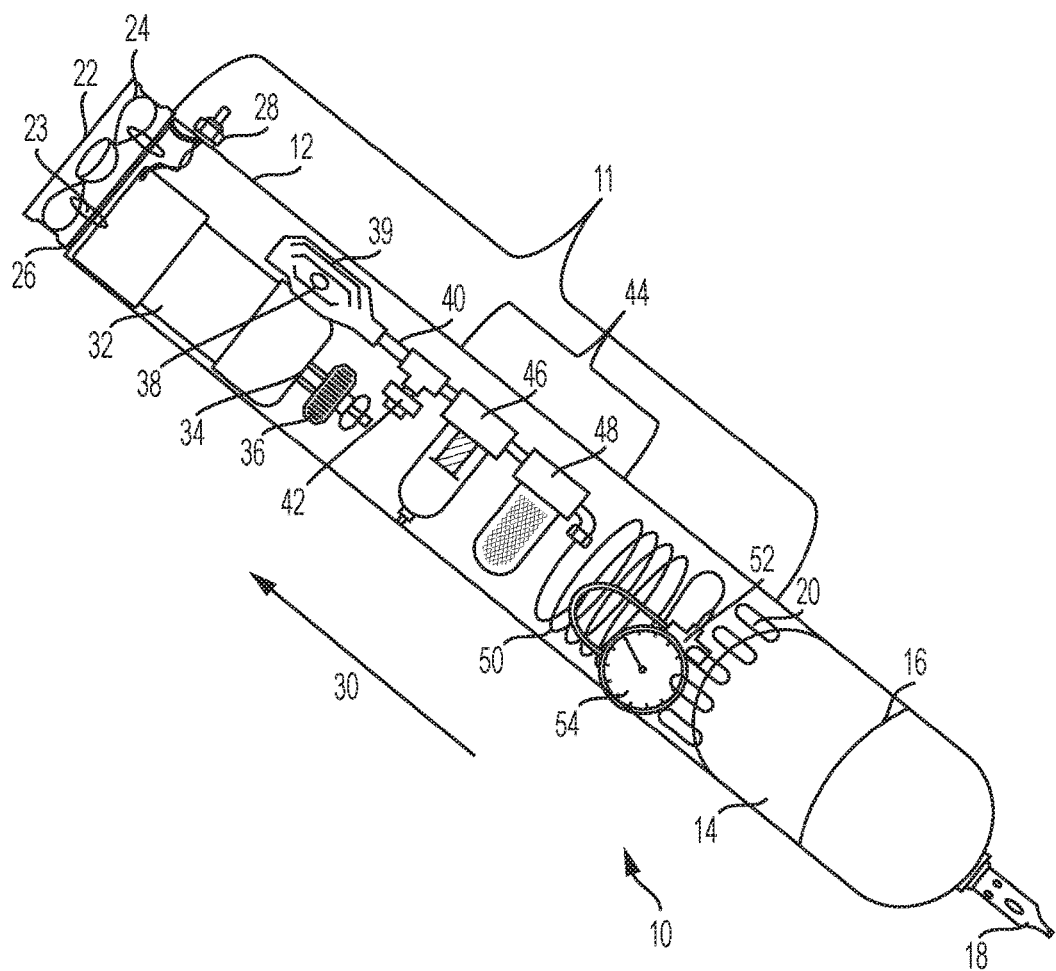
FIG. 1A is a perspective view of the apparatus according to invention principles.

In accordance with invention principles, an apparatus comprising a portable medical air compressor is provided. The apparatus advantageously provides a continuous source of medical grade breathing air to a patient. The apparatus is also easily transportable within a healthcare enterprise such as between units in a hospital. Additionally, the apparatus should be easily transportable between locations thereby advantageously enabling an emergency responder to have a continuous source of medical grade air when transporting patients to and from hospitals. The apparatus is advantageously configured to include all of the elements of a medical air compressor arranged to fit within a housing having the same size, shape and dimensions as a conventional medical gas cylinder that stores a finite amount of medical grade air therein. The apparatus includes a housing that houses the elements that comprise the medical air compressor and advantageously includes a plurality of intake apertures extending through the housing that allow air to flow therethrough and into the housing. An axial air flow generator is connected at an end of the apparatus that advantageously draws air through the intake apertures for processing by the elements of the medical air compressor to produce medical grade air which is stored in a refillable reservoir and which can be dispensed to a patient in need.

Turning now to the drawings, in which similar reference characters denote similar elements throughout the several views, FIGS. 1A through 8 illustrate an embodiment of the present invention.

An exemplary apparatus for providing a continuous supply of medical grade air is shown in FIG. 1A. The apparatus 10 includes a portable medical air compressor 11 designed to fit within a form factor associated with a conventional refillable medical gas cylinder advantageously enabling transport and usage in a plurality situations that heretofore have made use of the refillable medical gas cylinder. The apparatus 10 includes a housing 12 that is rigid and substantially tubular/cylindrical in shape so as to encapsulate the components of a medical air compressor 11 as discussed below. In one embodiment, the housing may be formed of a polycarbonate material that has dimensions substantially equivalent to a standard E size medical gas cylinder such that a diameter of the housing is substantially 4.375 inches by a length of substantially 29.5 inches. The material and dimensions are described for purposes of example only and the housing may have a size and shape substantially equivalent to any standard size medical gas cylinder and also may be formed from any material including metal. In another embodiment, the polycarbonate material is at least partially see-through thereby providing a view of the components contained therein.

A reservoir 14 is positioned at and extends at least partially from a first end 16 of the housing 12. The reservoir 14 may be substantially oval in shape and the portion extending from the first end 16 of the housing 12 forms the top rounded edge commonly associated with the shape and size of a medical gas cylinder. The reservoir 14 may be formed of any material that is capable of resisting the pressures induced by the medical air compressor 11 including but not limited to carbon fiber, steel, stainless steel and aluminum. The reservoir 14 may be connected to the medical air compressor 11 in the manner described hereinbelow. A valve 18 for dispensing medical air from the reservoir 14 is connected thereto using known techniques to prevent leakage of gas from within the reservoir. For example, the plumbing connection between the valve 18 and the reservoir 14 may be made by swaged, compression, and National Pipe Thread (NPT) type fittings to prevent leakage. While this type of plumbing connection is discussed with respect to the valve 18 and reservoir 14, one skilled in the art would recognize that these techniques may be employed for any and all plumbing connections made between any components of the apparatus 10 described hereinbelow. The valve 18 may be releasably connected to a conventional regulator (not shown) enabling the medical grade air stored in the reservoir 14 to be provided to the user in a known manner. The valve 18 may incorporate appropriate valves intended for use in their appropriate countries and comply with valve standards set by any of the Compressed Gas Association (CGA), Association Française de Normalisation (AFNOR), AGA gas company standards, Deutsche Institut fur Normung (DIN), and Ente Nazionale Italiano di Unificazione (UNi).

The housing 12 further includes at least one aperture 20 extending at least partially around the circumference of the first end 16 of the housing 12 and provides an inlet for ambient air to enter the housing 12. The at least one aperture 20 may be of any shape and size capable of allowing air to be drawn therethrough. In one embodiment, the at least one aperture 20 includes a plurality of apertures in a band extending at least partially around the circumference of the first end 16 of the housing 12. In another embodiment, the at least one aperture 20 may be covered with a screen or other filtering material preventing large particulate matter from entering the housing 12. The band of apertures 20 are positioned at a predetermined distance from the first end 16 of the housing 12. The distance of the apertures 20 from the first end of the housing 12 is determined by a length of the reservoir 14 that extends within the housing 12. The apertures 20 should not be obstructed by the reservoir 14 and provide a clear path for the ambient air to flow therethrough. The location of the band of apertures 20 may be upstream from the components of the medical air compressor 11. In one embodiment, the band of apertures 20 may be positioned substantially over and around a connection point between the medical air compressor 11 and the reservoir 14 thereby providing complete and unobstructed path for ambient air to flow into the housing 12.

An air flow generator 22 is positioned adjacent a second end 24 of the housing 12. The air flow generator 22 may be at least one of (a) a fan, (b) a pump and (c) a vacuum. However, one skilled in the art will appreciate that the air flow generator may be any device able to create a flow of air in a desired direction. The embodiment described herein depicts the air flow generator 22 as a fan. The air flow generator 22 receives power from a power connector 28 and may be separated from the inner section of the housing 12 by a grate or screen 26. The grate or screen 26 may be positioned on a side of the air flow generator 22 opposite the second end 24. The housing 12 may also include at least one exhaust apertures 23. The at least one exhaust aperture 23 may also include a plurality of exhaust apertures 23 that extend at least partially around the circumference of the second end 24 of the housing 12 in a band and provide an egress port for air to exit the housing 12. The exhaust apertures 23 may be of any shape and size capable of allowing air to be drawn therethrough. In one embodiment, the exhaust apertures 23 may be covered with a screen or other filtering material preventing large particulate matter from entering the housing 12 and disrupting operation of the air flow generator 22. The band of apertures 20 are positioned at a predetermined distance from the second end 16 of the housing 12. In one embodiment, the exhaust apertures 23 may be positioned between the air flow generator 22 and the second 24. In another embodiment, a second set of exhaust apertures (shown in FIG. 9) may be positioned on the second end 24 of the housing 12 allow the air from within the housing 12 to exit therefrom.

The air flow generator 22 rotates so as to draw ambient air through the plurality of apertures 20 into the housing 12 in a direction represented by the arrow labeled with reference numeral 30. The air flow generator 22 may be of any shape or size to provide a minimum air flow rate of 100 cubic feet per minute (cfm). The ambient air is drawn by the air flow generator 22 into the housing 12 and flows over and around the components that comprise the medical air compressor 11 and enable the medical air compressor 11 to operate as intended as well as to provide a continuous source of air on which the medical air compressor 11 can process into medical grade air. The air flowing over and around the components of the medical air compressor 11 may exit the housing via the at least one exhaust aperture 23. In one embodiment, the operation of the air flow generator 22 may be selectively controlled by a user. In another embodiment, air flow generator operation may be controlled by a control circuit (not shown) that selectively causes the air flow generator 22 to operate in response to a predetermined condition. In one embodiment, the air flow generator 22 may be operational during predetermined time intervals whereby the air flow generator 22 is operational for a first time period and not operational during a second time period (the first and second time periods may or may not be of the same duration). In another embodiment, the air flow generator 22 may be controlled to operate at a predetermined time or set of times during the day. In a further embodiment, the air flow generator 22 may automatically operate in response to detecting a decrease in pressure in the reservoir 14 indicating that the medical air is being dispensed to a patient. Another embodiment may include the air flow generator 22 automatically operating when a pressure in the reservoir 14 falls below a first threshold value and ceasing to operate when a pressure in the reservoir 14 reaches a second threshold value. In this embodiment, the first and second threshold values may be the same or different pressure.

The configuration and position of the medical air compressor 11 within housing 12 will now be described. A compressor 32 capable of compressing air to at least 100 psi is provided and positioned within the housing 12 adjacent the second end 24 thereof. The compressor 32 may be an oil-less compressor which advantageously enable the compressor to comply with the low hydrocarbon requirement for medical grade air. The compressor 32 is electrically connected to the power connector 28. The power connector 28 may provide power from a power source (not shown) to the compressor 32 and the air flow generator 22. The power source may include a dedicated outlet and/or battery pack. The compressor 32 includes an intake port 34 for receiving air to be compressed and an output port 38 through which compressed air is provided to the remaining components of the system. A particle filter 36 is connected to the intake port 34 of the compressor 32. The particle filter 36 filter provides 99.999% filtration of bacterial and viral pathogens that may be present in the ambient air being drawn into the housing 12 by the air flow generator 22 and represents a first stage of filtering required to produce medical grade air. In one embodiment, the particle filter 36 is able to filter bacterial and viral particles greater than 0.3 μm in size. In operation, the air flow generator 22 rotates and draws ambient air into the housing 12 which is filtered by the particle filter 36 prior to entrance into the compressor 32 via the intake port 34. The compressor 32 compresses the air to a predetermined pressure and the compressed air is output via the output 38.

The compressed air exits the compressor 32 via the output port 38 and is sent through a compressor head 39 and further through a check valve 40 to prevent blowback through the compressor 32. A pressure switch assembly 42, set to a threshold pressure in the reservoir 14, is fitted to the check valve 40 at the output port 38 of the compressor 32. The pressure switch assembly 42 is electrically connected to the compressor 32 and the air flow generator 22. Upon the pressure in the reservoir 14 reaching the threshold pressure, the pressure switch assembly 42 moves from a first closed position to a second open position and automatically disconnects the air flow generator 22 and the compressor 32 from the power source. When the pressure in the reservoir 14 falls below the threshold pressure, the pressure switch assembly 42 moves from the second open position into the first closed position connecting the air flow generator 22 and compressor 32 with the power source. The location of the pressure switch assembly 42 is shown for purpose of example only and the pressure switch assembly 42 may be located at any position within the circuit downstream from the check valve 40.

A filtration unit 44 is connected to the pressure switch assembly 42 and provides a second stage of filtration required to produce medical grade air. The filtration unit 44 may include a plurality of individual filters for performing different filtering functions. As shown in FIG. 1A, the filtration unit 44 includes a standard air line oil/water separation device (e.g. coalescing filter) 46 that removes oil, water and other particulate matter from the compressed air. The filtration unit 44 may also include a standard desiccant dryer 48 to further dry the compressed air. Thus, the output of the desiccant dryer 48 is clean dry air. The oil/water filter 46 and the desiccant dryer 48 are connected in series. The arrangement of the oil/water filter 46 and desiccant dryer 48 advantageously enables the filtration unit 44 to trap any water from the system prior to additional gas filtering or scrubbing which prevents the moisture from contaminating the adsorption material in the down stream gas scrubbers. In another embodiment, the filtration unit 44 may further include a gas conditioning system to ensure that the compressed air is medical grade. An exemplary gas conditioning system may include at least one gas scrubbing device for removing a particular type of element from the gas passing therethrough. The at least one gas scrubbing device may be able to remove at least one of carbon monoxide (CO) and carbon dioxide ($CO_2$) from the compressed air passing therethrough. The gas scrubbing device may remove the CO and/or $CO_2$ using any of calcium oxide, a polymer membrane, lithium oxide or some other known catalyst. In one embodiment, a carbon monoxide oxidation catalyst converts CO to $CO_2$ which can be removed from the compressed air by calcium Oxide. The filtration unit 44 may also include a carbon dioxide scrubber that removes any carbon dioxide from the compressed air and/or a carbon monoxide monitor for monitoring the presence of carbon monoxide in the compressed air flowing therethrough. If carbon monoxide is detected, the apparatus may employ the carbon monoxide oxidation catalyst to convert the carbon monoxide to carbon dioxide. Alternatively, the source of carbon monoxide may be eliminated or the gas scrubber may be recharged or renewed.

The output of the filtration unit 44, shown herein as the output of the desiccant dryer 48, is connected to a cooler assembly 50. Compressed air flows through the cooler assembly 50 in order to dissipate heat generated during the compression process. The cooler assembly 50 may be formed from any material capable of supporting the pressures induced by the compressor 32. In one embodiment, the cooler assembly 50 may be formed from a plurality of copper coils which are employed because copper is an excellent microbial inhibitor and also possesses a high degree of thermal conductivity which improves the heat dissipation process. The cooling performed by the cooling assembly 50 is further aided by the operation of the air flow generator 22 drawing ambient air from outside of the housing through the apertures 20 causing the ambient air, which has a lower temperature as compared to the compressed air, over and around the cooling assembly 50 to further aid in the heat dissipation processor. Thus, the orientation and position of the band of apertures 20 enhance the cooling process needed in order to store the compressed air in the reservoir 14. The constant influx of cooler ambient air drawn into the housing 12 by the air flow generator enables the apparatus to continuously replenish the medical grade air provided by the apparatus while preventing the components of the medical air compressor 11 (e.g. the cooling assembly 50 and compressor 32) from overheating.

A T-connector 52 (e.g. a ¼" NPT Tee) is connected at an output of the cooler assembly 50. A first branch of the T-connector 52 is connected to the output of the cooler assembly 50. A pressure gauge 54 is connected to a second branch of the T-connector 52 which enables a user to view the pressure of the gas contained therein. An input to the reservoir 14 is connected to a third branch of the T-connector 52. The pressurized medical grade air is provided from the cooler assembly 50, through the third branch of the T-connector 52 into the reservoir 14. In one embodiment, the housing 12 maybe formed entirely of a see-through material providing visual access to the pressure gauge 54 and all other components of the apparatus 10. In another embodiment, the housing 12 may be partially see-through providing visual access only to the pressure gauge 54.

Thus, the apparatus 10 provides a closed system that provides a continuous supply of medical grade air derived from ambient air being drawn through the band of apertures 20 and into the housing 12. The air drawn into the housing 12 by the axial air flow generator 22 is used as an input air source for the medical air compressor 11 as well as to cool components of the medical air compressor 11. This operation is enabled as a direct result of the position of the band of apertures 20 with respect to the cooler assembly 50 and compressor 32 of the medical air compressor 11.

In operation, power is provided to the apparatus via the power connector 28 which energizes the air flow generator 22 and compressor 32. The apparatus may operate using any of 12 VDC, 24 VDC or 120 VAC or 230 VAC. The air flow generator 22 rotates causing ambient air surrounding the apparatus 10 to be drawn through the plurality of apertures 20 in the housing 12. The air undergoes the first stage of filtration via the particle filter 36 prior to compression. The compressor 32 compresses the air to a predetermined pressure (psi). The compressed air flows through the pressure switch assembly 42. It is important to note that, upon initial filling of the reservoir 14 as described herein, the pressure switch assembly 42 is in the second closed position thereby completing a circuit between it, the power source (via the power connector 28), the compressor 32 and the air flow generator 22. The compressed air then flows through the components of the filtration unit 44. In the oil and water filter 46 (e.g. a course filter) of the filtration unit 44, oil, water and particulate matter are removed from the compressed air which then flows through the desiccant dryer 48 for further drying to remove any residual ambient moisture in the compressed air. Upon exiting the desiccant dryer 48, the compressed air flows through the cooler assembly 50 in order to dissipate heat generated by compression thereof. The heat dissipation is enhanced by the continuous influx of ambient air resulting from the air flow generator 22 drawing the air through the plurality of apertures 20 which flows around the cooler assembly 50. The ambient air has a temperature lower than a temperature of the compressed air as it enters the cooler assembly 50 which improves the heat dissipating effects of the cooler assembly. The improved cooling results directly from the arrangement of the components within the housing 12 such that the cooler assembly 50 is intentionally positioned downstream (with respect to the flow of air indicated by arrows 30) from the plurality of apertures. The cooled compressed air exits the cooler assembly 50 and flows through the T-connector 52 into the reservoir 14 to create a store of medical grade air that may be provided to a patient, as needed, via the valve 18. Additionally, the compressed air flows through the T-connector 52 and is monitored by the pressure gauge 54 which provides a user with an indication of the pressure level within the reservoir 14.

The components of the medical air compressor 11 positioned within the housing 12 may be selectively removable from the housing 12. By providing access to the components, a user is able to easily service and maintain the medical air compressor 11. For example, the components may be removable to allow a user to replace, recharge or otherwise service the filtration unit 44 or the particle filter 36. Thus, any service necessary to maintain the apparatus in a working condition may be performed. To affect the removability of the components, the components may be mounted on an internal structure that can be accessed through the housing 12 and removed therefrom. The mounting structures and manner in which they enable the components to be removed from the housing 12 will be discussed below with respects to FIGS. 1B-1E.

For purposes of discussion associated with the mounting apparatus shown herein, the air flow generator 22, medical air compressor 11 and reservoir 14 will be collectively referred to as internal components. One skilled in the art would appreciate that any element described in FIG. 1A that may be positioned within the housing 12 may also be considered an internal component. Additionally, one skilled in the art understands that each respective internal component may be mounted to the mounting structure in a manner known to be associated with the respective component. Moreover, it should be appreciated that the internal components may be mounted directly to the mounting structure or mounted on the mounting structure using a stilt or peg or other device able to create a space between the component and the mounting structure.

Figure 1B:
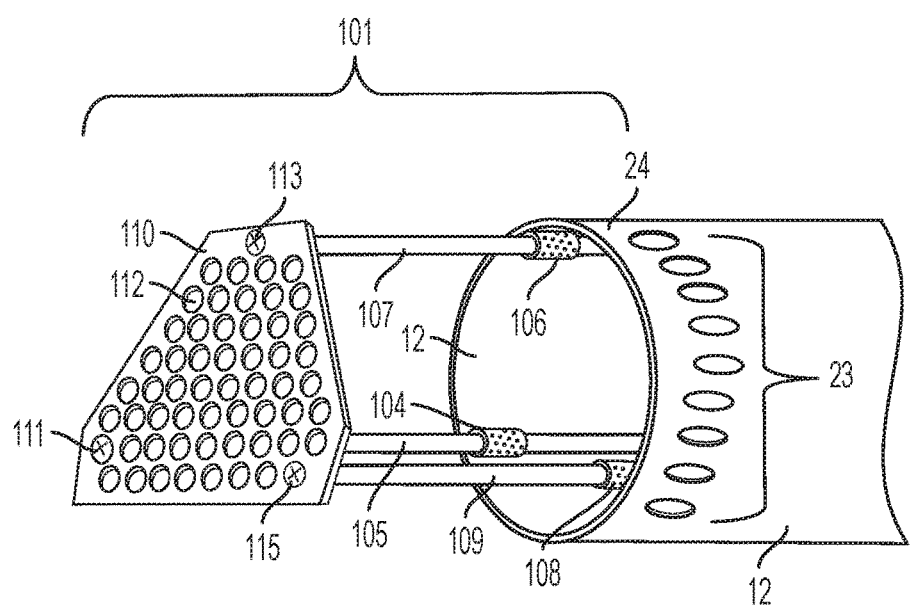
FIG. 1B is a side view of the apparatus including an exemplary mounting structure for internal components according to invention principles.

FIG. 1B is a side view of the apparatus 10 shown in FIG. 1A and depicts an exemplary mounting structure 101 for the internal components of the apparatus 10. Shown herein is the second end 24 of the housing 12 which includes the plurality of exhaust apertures 23. Access to the internal components of the apparatus 10 is provided at the second end 24 of the housing 12. The mounting structure 101 is received through the second end 24 of the housing 12. The mounting structure 101 includes a plurality of sets of linear bearings 104, 106 and 108 and a plurality of rails 105 (a first rail), 107 (a second rail) and 109 (a third rail) that are received by respective ones of the sets of linear bearings 104, 106, 108. A rear plate 110 is connected to the plurality of rails 105, 107 and 109 in order to cover at least a portion of the second end 24 of the housing 12. The rear plate 110 is shown shaped as a pentagon. However, this is for purposes of example only and the shape of the rear plate 110 maybe any geometric shape enabling the rear plate to allow connection to the second end of the housing 12. Additionally, the rear plate may include a plurality of rear exhaust apertures extending therethrough in order to provide additional avenues for air within the housing 12 to exit. The number of rails and sets of bearings shown herein is for purposes of example only and any number of rail and bearing combination may be employed so long as the internal components are able to be stably mounted thereon and easy access to the internal components is provided.

As shown herein, the housing 12 includes an inner surface 102. Positioned on the inner surface 102 of the housing 12 are a first set linear bearings 104, a second set of linear bearings 106 and a third set of linear bearings 108. Each set of linear bearings 104, 106 and 108 include at least two linear bearings positioned on the inner surface 102 of the housing 12 and aligned with each other thereby creating a track. A first end of the first rail 105 is connected to the rear plate 110 via connector 111. A second end of the first rail 105 is received by the first set of linear bearings 104. A first end of the second rail 107 is connected to the rear plate 110 via connector 113. A second end of the second rail 107 is received by the second set of linear bearings 106. A first end of the third rail 109 is connected to the rear plate 110 via connector 115. A second end of the third rail 109 is received by the third set of linear bearings 108. The combination of the rails and sets of bearings forms a stable track on which the internal components may be mounted. Thus, the mounting structure 101 is movable along a length of housing 12 and provides access to the internal components mounted thereon.

Figure 1C:
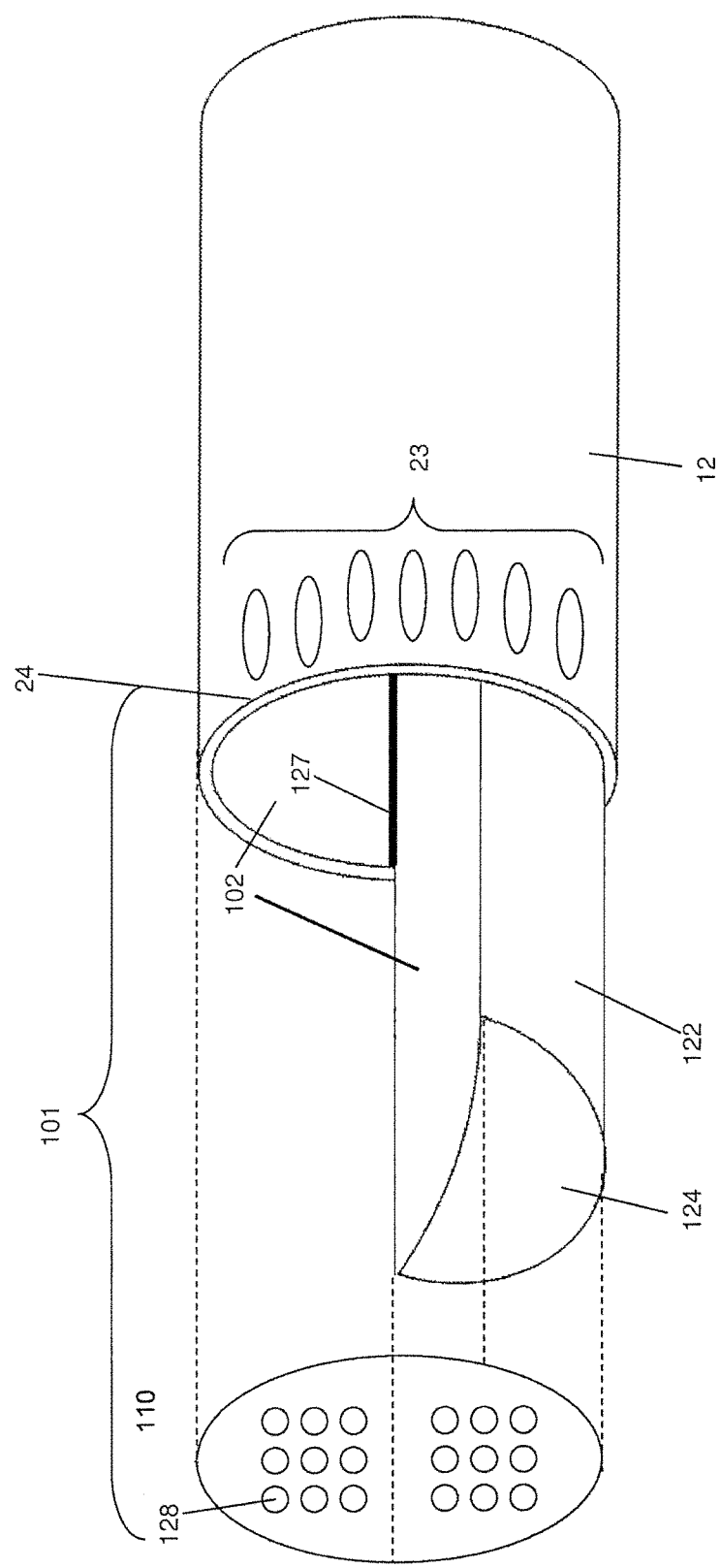
FIG. 1C is a side view of the apparatus including an exemplary mounting structure for internal components according to invention principles.

FIG. 1C is another exemplary mounting structure 101 for the internal components of the apparatus 10. Shown herein is the second end 24 of the housing 12 which includes the plurality of exhaust apertures 23. Access to the internal components of the apparatus 10 is provided at the second end 24 of the housing 12. Positioned on an inner surface 102 of the housing are guide rails 127 that may extend along a length of the inner surface 102 of the housing 12. The mounting structure 101 is received through the second end 24 of the housing 12. The mounting structure 101 includes a tray 122 having an inner surface 102 on which the internal components may be mounted. The tray 122 may be semi-circular in shape and have a length substantially the same as a length of the housing 12. The tray may also include at least one aperture extending therethrough to enable air to flow in a space between the tray 122 and the inner surface 102 of the housing 12. The tray 122 is received under the guide rails 127 thereby providing a track on which the tray 122 may slide thus allowing the tray to traverse the length of the housing 12 and provide access to the components mounted thereon. This advantageously maintains the position of all internal components so that they do not rotate around the inner surface 102 of the housing 12. In one embodiment, the internal components are mounted directly to the tray 122. In another embodiment, the internal components may be mounted using pegs or lifts thereby creating a space between the internal mounted components and the inner surface 102 of the tray increasing the pathway for air to flow. The mounting structure 101 further includes a rear plate 110 having a plurality of rear exhaust apertures 128. The exploded view of FIG. 1C shows that the rear plate 110 is connected to a first edge 124 of the tray 122 as well as to the second end 24 of the housing 12. The rear plate 110 may have substantially the same dimensions as the opening of the second end 24 of the housing 12 enabling a tight fit. The rear plate may be connected to both the tray 122 and the housing 12 by any connector. In one embodiment, the rear plate may include a thickness with threading extending therearound and the housing may include matching threads enabling the mounting structure 101 to be secured to the housing by being screwed thereon. In another embodiment, the rear plate 110 may be connected to the tray 122 and the housing 12 by a screw or other type of fastener.

Figure 1D:
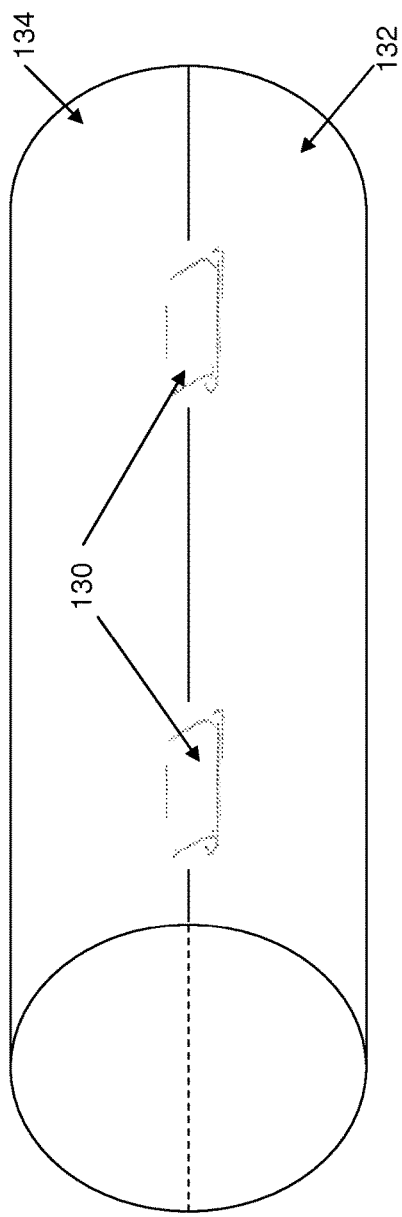
FIGS. 1D & 1E are side views of the housing able to provide access to internal components according to invention principles.
Figure 1E:
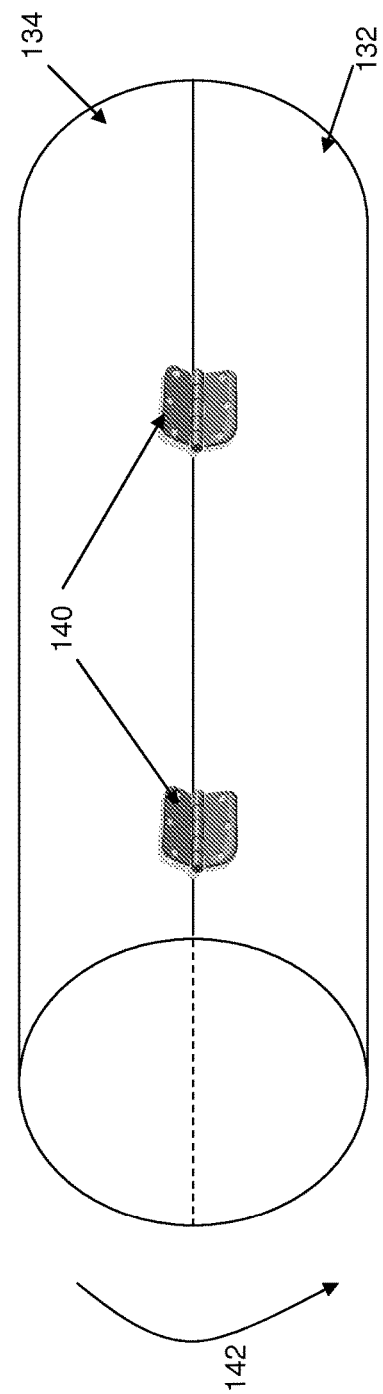

FIGS. 1D and 1E are opposing side views of an alternative housing 12 for use with the apparatus 10. The housing 12 includes a first section 132 and a second section 134. The first section 132 and second section 134 are both semi-circular in shape and when connected to one another form the cylindrical housing 12 discussed above in FIG. 1A. The first section 132 may be connected to the second section 134 by a plurality of hinges 140. The first and second sections 132 and 134 are further held together by a plurality of reliable latches 130 as shown in FIG. 1D. Upon release of the latches 130, the first section 132 and second section 134 pivot about the hinges 140 in a direction shown by the arrow labeled 142 in FIG. 1E. Upon pivoting about the hinges 140, access to the inner surface 102 of the first section 132 and second section 134 is provided. The housing shown herein may be used with any of the mounting structures 101 shown in FIGS. 1B and 1C. In another embodiment, no mounting structure is required and the internal components may be mounted directly to either the inner surface of the first section 132 or the second section 134.

Figure 2:
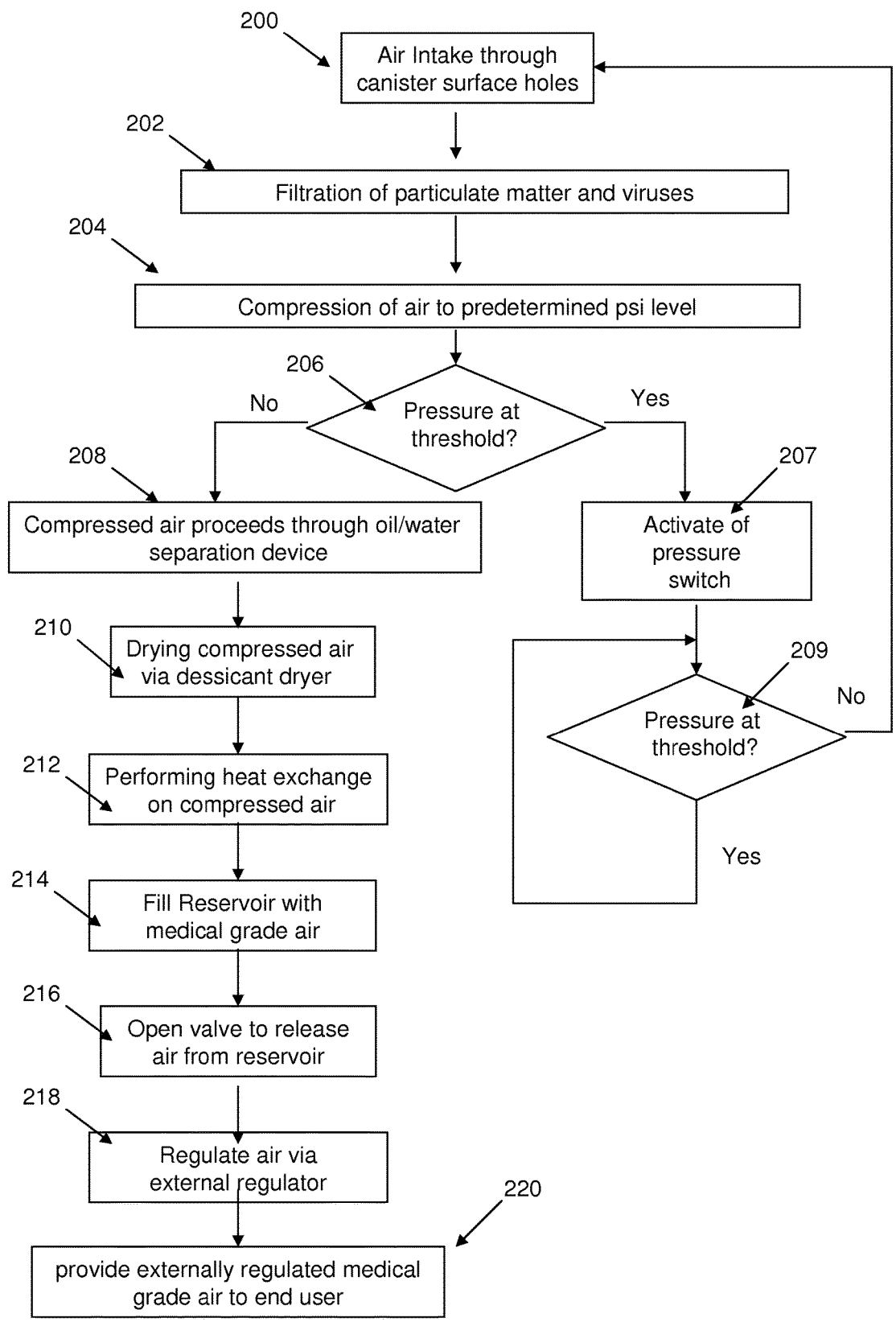
FIG. 2 is the flow diagram detailing the operation of the apparatus according to invention principles.

FIG. 2 shows a flow diagram detailing the pathway of air flow through the apparatus shown in FIG. 1A. In step 200, ambient air surrounding the apparatus 10 is drawn through the plurality of apertures 20 on the wall of the housing 12 by the air flow generator 22. The air flows within the housing 12 and over and around the cooler assembly 50, the pressure gauge 54, the filtration unit 44 and the pressure switch assembly 42 until it reaches the particle filter 36 which is adjacent the pressure switch assembly 42 and the compressor 32. The air is filtered by the particle filter 36 to remove bacterial and viral particles in step 202. The compressor 32 receives the filtered air and compresses the air in step 204. In step 206 the pressure switch assembly determines if the pressure in the system has reached a threshold pressure. If the pressure has reached the threshold pressure, the pressure switch assembly 42, in step 207, is caused to move from the first closed position to the second open position interrupting the electrical circuit formed by the pressure switch assembly 42, the air flow generator 22, the compressor 32 and the power source to cease operation of the air flow generator 22 and the compressor 32. In step 209, a determination is made as to the pressure in the system and, if the pressure has fallen below the threshold level, the pressure assembly switch moves from the second open position into the first closed position in step 211 and operation returns back to step 200 whereby the air flow continues.

If, in step 206, it is determined that the pressure level has not reached the threshold pressure, the compressed air proceeds through the oil/water (course) filter in step 208 and is dried by the desiccant dryer in step 210. Air exiting the dryer in step 210 enters the cooler assembly in step 212 in order to dissipate the heat generated by compression of the air. The activity in step 212 is aided by the air being drawn into the housing 12 in step 200 which has a temperature lower than a temperature of the compressed air and which flows over and around the cooler assembly 50. The improved cooling is a direct result of the orientation of the cooler assembly 50 downstream from the plurality of apertures 20 in the housing 12 with respect to the direction of air flow within the housing 12. The cooled, clean compressed medical grade air flows into the reservoir 14 in step 214. Air in the reservoir 14 is dispensed for use in step 216 wherein the valve 18 is connected to a regulator. The valve is opened and air flowing into the regulator is regulated in step 218 and provided to a user in step 220.

Figure 3:
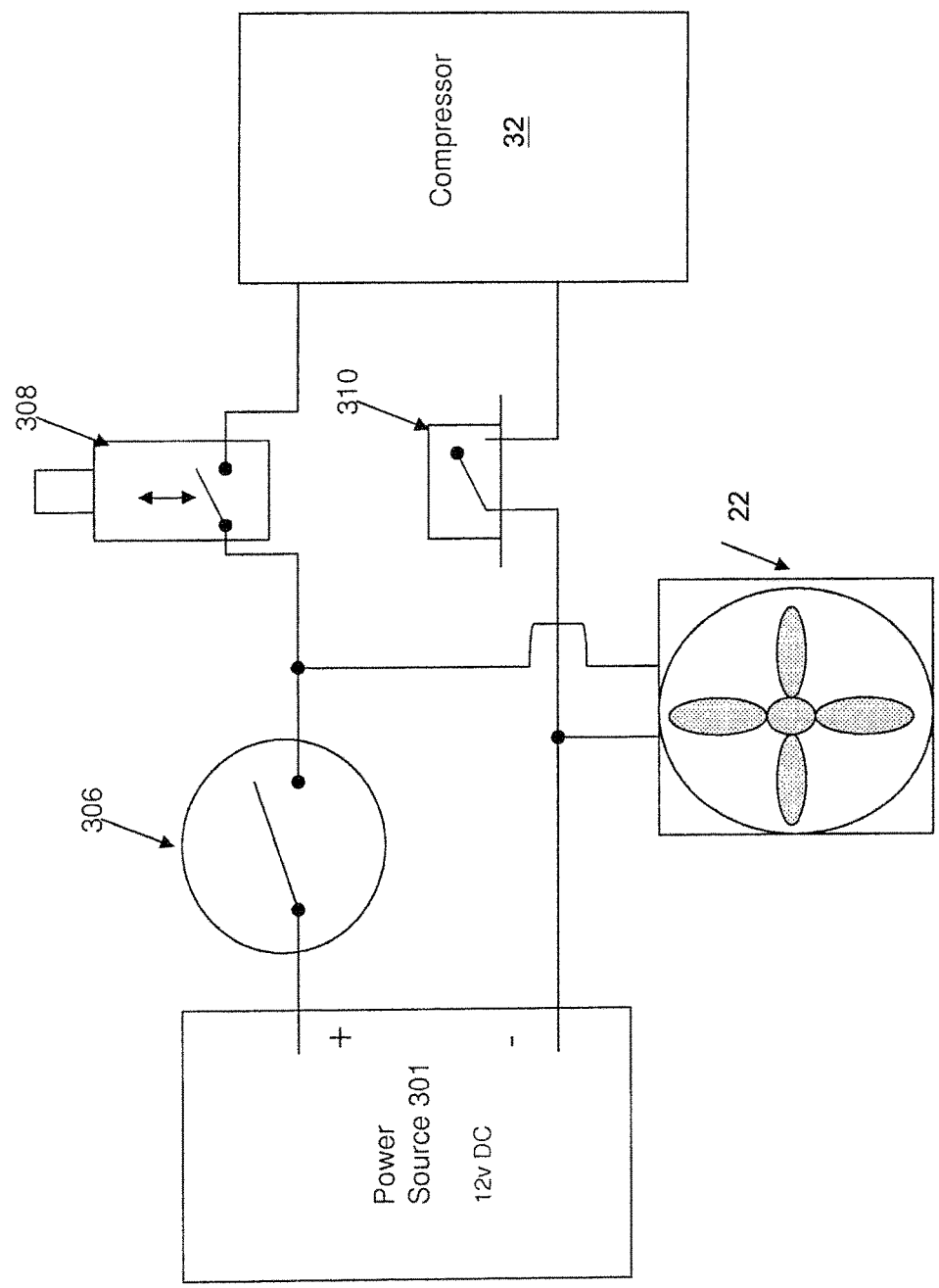
FIG. 3 is an electrical block diagram of the apparatus according to invention principles.

FIG. 3 is an electrical block diagram for the apparatus of FIG. 1A. As discussed above and shown herein, the components of the apparatus that require power from a power source are the air flow generator and the compressor. The electrical operation of the apparatus is being discussed with respect to FIG. 3 and, one skilled in the art should appreciate that despite being depicted with different reference numerals, like-named components may be the same components discussed above with respect to FIG. 1A.

A power source 301 may provide a 12V power input could be 24 VDC, 120 VAC, or 230 VAC to the compressor 32 and the air flow generator 22. The power source may include (a) a 12 VDC power source (b) a 12 VAC power source along with an AC/DC conversion unit, (c) a rechargeable DC battery pack and (d) a rechargeable AC battery pack with an AC/DC converter contained therein. The compressor 32 and air flow generator 22 operate in a similar manner as discussed hereinabove with respect to FIG. 1A. A plurality of switches are disposed within the circuit and, depending on their positioning, control whether or not the circuit is completed and power provided to the compressor 32 and the air flow generator 22. The circuit includes a power switch 306 enabling a user to determine if the power should be applied to the air flow generator 22 and compressor 32. A pressure switch 308 is provided for automatically sensing a pressure in a reservoir (14 in FIG. 1A) to determine if a threshold pressure has been reached. The pressure switch 308 is selectively settable by a user to any predetermined pressure value. A thermistor 310 is provided and is coupled to the compressor 32 for selectively detecting a temperature of the compressor 32 ensuring that the compressor 32 does not over heat. The thermistor 310 may also monitor a temperature of the gas to prevent thermal damage to users, patients, or equipment. Alternatively, in addition to or instead of the thermistor 310, the apparatus may include a thermocouple or other temperature sensor to monitor the temperature of at least one of the compressor 32 and the gas. When any of the switches 306, 308 are in the first open position, the circuit is incomplete and the apparatus is turned off. When all of the switches are in the second closed position, the circuit is completed and the apparatus is operational. The different switch operations and orientations are discussed below.

Prior to operation, the power switch 306 is in the first open position and pressure switch 308 and thermistor 310 are in the second closed position. When in the power switch 306 is in the first open position, no power is provided to the compressor 32 or the air flow generator 22 and the apparatus is not operating. Upon actuation of the power switch 306, the switch moves from the first open position to the second closed position completing the electrical circuit and providing power to the air flow generator 22 and compressor 32. The air flow generator 22 draws air in through the plurality of apertures in the housing for compression by the compressor 32. This air is then filtered and compressed and used to fill the reservoir 14 with medical grade air as discussed with reference to FIGS. 1A and 2. This operation continues until the pressure switch 308 senses that the pressure in the reservoir has reached a threshold pressure. Upon determining that the pressure in the reservoir reached the threshold, the pressure switch 308 moves from the second closed position to the first open position thereby interrupting the circuit and causing the apparatus to stop operating. It is important to note that, the power switch 306 may remain in the second closed position thereby ensuring that when the pressure in the reservoir falls below the threshold and the pressure switch 308 returns to the second closed position, the circuit is complete once again and the apparatus may continue to operate and draw air into the housing thereby advantageously providing a continuous, refillable source of medical grade air.

In parallel with the pressure switch 308, a thermistor 310 continuously monitors a temperature of the compressor 32 to ensure that the compressor 32 is operating within an acceptable temperature range. The compressor 32 is cooled during operation as a result of the cooler ambient air that is being drawn into the housing by the air flow generator 22. In addition to providing a supply of air for compression by the compressor 32, the air drawn into the housing by the air flow generator acts as a coolant to the compressor 32 and a cooling assembly that cools the compressed air prior to storage in the reservoir. This cooler ambient air aids in cooling the compressor 32 during operation. Thus, the thermistor is a fail-safe that checks to make sure that the apparatus is operating as intended. Should the temperature of the compressor 32 reach a threshold temperature value, the thermistor 310 automatically moves from the second closed position to the first open position and interrupts the electrical circuit causing the apparatus to stop operating. If this occurs, both the power switch 306 and the pressure switch 308 may remain in the second closed position thereby enabling the circuit to be completed when the thermistor 310 senses that the compressor 32 temperature has fallen below the threshold value.

In another embodiment, the circuit shown in FIG. 3 may also include a relay coupled to the power switch 306 that selectively senses an externally generated control signal. In response to sensing the externally generated control signal, the relay could automatically cause the power switch 306 to move from the first open position to the second closed position thereby completing the circuit and causing the apparatus to operate (provided that switch 308 is also in the second closed position). Thus, the apparatus may be selectively coupled with an another component and operate in response to a control signal generated by the component. In one embodiment, the additional component may be a patient monitoring device that monitors at least one type of parameter associated with the patient. The patient monitoring device may sense that the monitored patient parameter has at least one at least one of reached, exceeded or fallen below a threshold value thus requiring the patient to receive a supplemental source of medical grade air. The patient monitoring device may generate a control signal that is sensed by the relay causing the power switch 306 to move from the first open position to the second closed position thereby causing the apparatus to operate as discussed above. It should be appreciated that the apparatus may receive a second control signal from the patient monitoring device causing the power switch 306 to move from the second closed position to the first open position ceasing operation. In one embodiment, the patient monitoring device may be an oximeter that monitors an amount of oxygen in a patient's blood and, if the oximeter determines that the amount of oxygen is below a threshold, the oximeter may generate the control signal and provide the signal to the apparatus. The relay in the apparatus may sense the control signal and cause the apparatus to operate and provide additional medical grade air to the patient to remedy the detected low-oxygen condition. One skilled in the art understands that the relay may receive the signal via wired or wireless connection.

Figure 4:
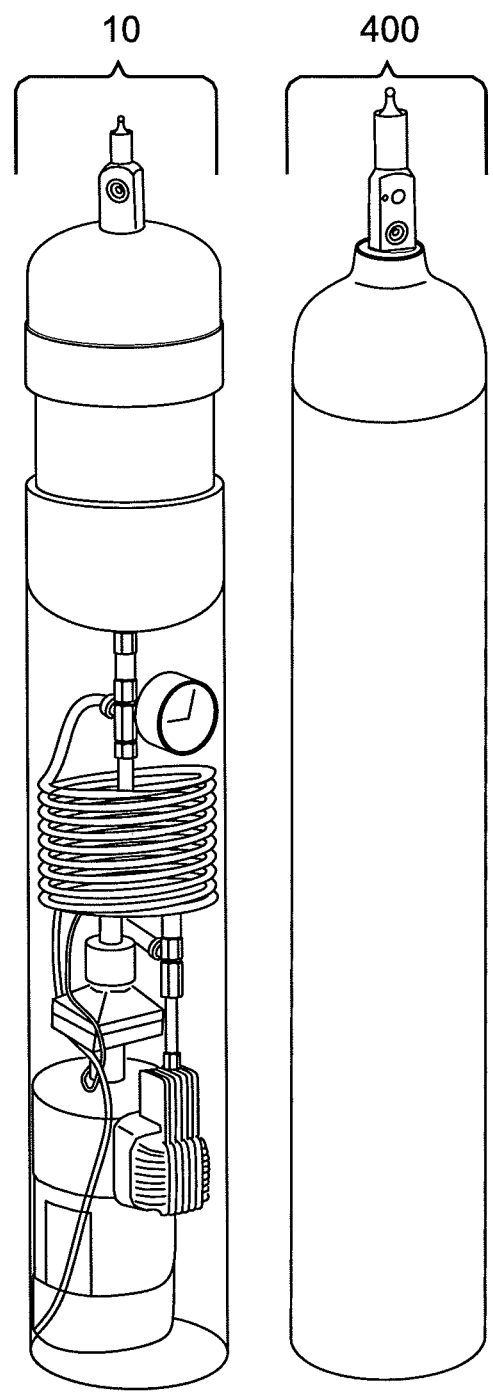
FIG. 4 is a depiction of the apparatus according to invention principles alongside a conventional medical gas cylinder.

FIG. 4 shows the apparatus 10 described above with respect to FIGS. 1A-3 along side a conventional medical gas/air cylinder 400. As can be seen, the apparatus 10 is configured in such a manner to arrange the components of a medical air compressor which, heretofore has taken on the form factor of a suitcase, into a housing having substantially the same dimensions as a cylinder for storing and supplying medical grade air. Moreover, the apparatus provides an improvement over conventional medical air compressors by efficiently arranging the components within a housing of the apparatus thereby enabling the apparatus to have a form factor substantially the same as the medical air cylinder. Additionally, the apparatus advantageously provides a continuous source of medical grade air by using the surrounding ambient air as both an input air source as well as a source of cooling that automatically cools various components of the medical air compressor and enables these components to operate within an acceptable temperature range while arranged in the manner described herein. Without the apertures allowing air to enter the housing and being positioned upstream from the components, the apparatus would not be an efficient an acceptable source of medical grade air. Thus, the apparatus provides medical professionals with a continuous source of medical grade air in a convenient and widely used form factor readily adaptable for sue with conventional devices thereby reducing the need to retrofit other medical apparatuses. The apparatus also advantageously reduces the time and effort needed to remove and replace conventional medical gas cylinders when their finite amount of gas is depleted.

Additionally, by providing the continuous source of medical grade air, the patient is not deprived of oxygen at any point during their treatment caused by the need to replace conventional medical gas cylinders.

Figure 5:
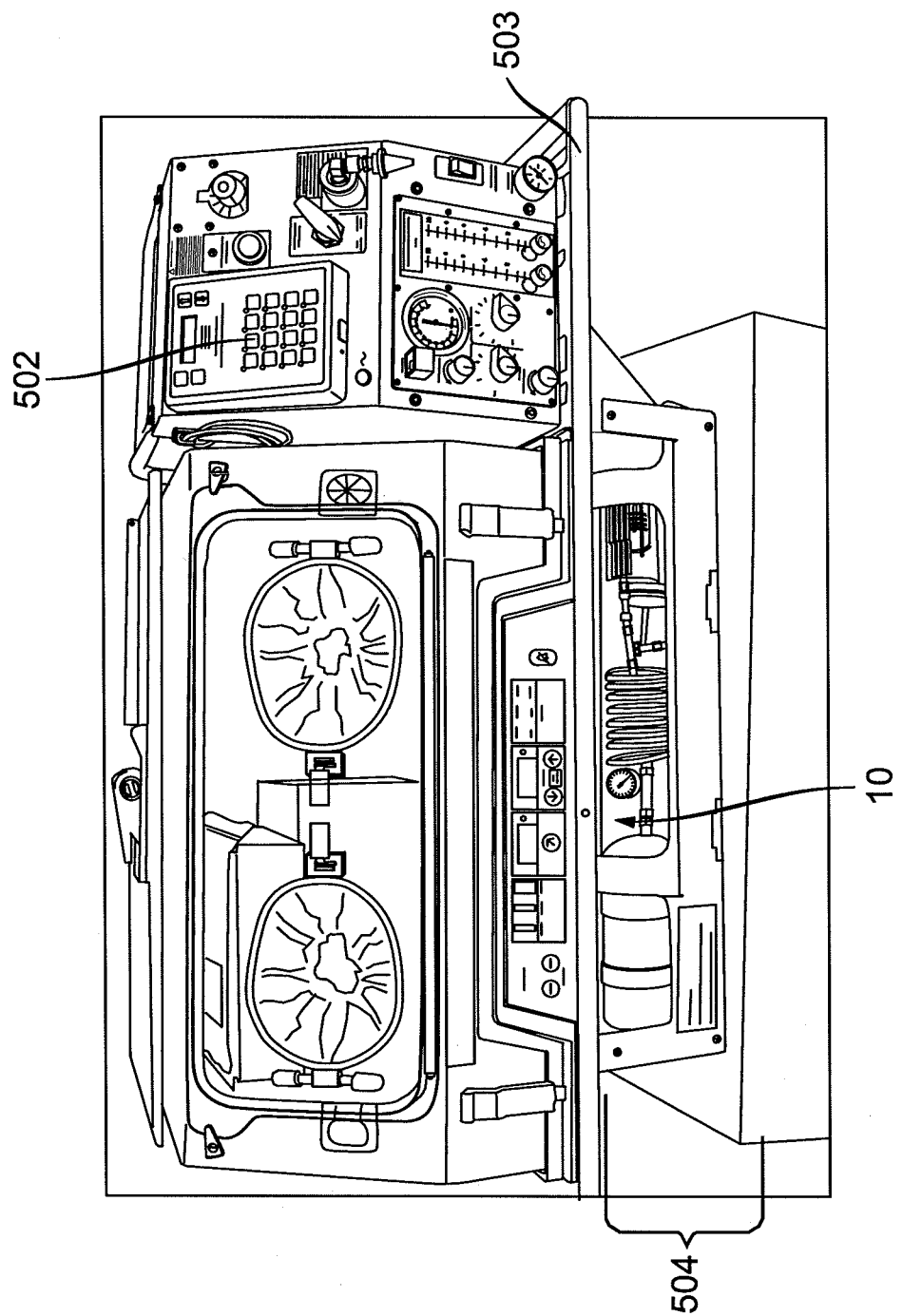
FIG. 5 is a side view showing an exemplary usage of the apparatus according to invention principles.

FIGS. 5-8 are different views of an exemplary environment in which the apparatus 10 may be used. FIG. 5-8 represent four views of an exemplary infant incubator that may be employed in a healthcare enterprise, for example in a neonatal intensive care unit. FIG. 5 shows a side view of a first side of an infant incubator 502 positioned on a platform 503. The operation and features of the infant incubator 502 are not germane to the present invention and will not be discussed further. The infant incubator 502 includes a first cylinder storage region 504 positioned on an underside of the platform 503 and may be a substantially rectangular shaped region that is able to receive a medical gas cylinder therein. As shown in FIG. 5, the apparatus 10 is retained within the first cylinder storage region 504 and is able to provide a substantially continuous supply of medical grade air to a neonatal patient in the incubator 502 as needed. As vent holes are located around the periphery of the incubator 502, installation will not completely block the air flow of the apparatus 10. The installation of the cylinder into the device is not an air tight fit but the apparatus 10 will be able to compensate for any decreased air flow based on the location at which the apparatus 10 is installed and used.

Figure 6:
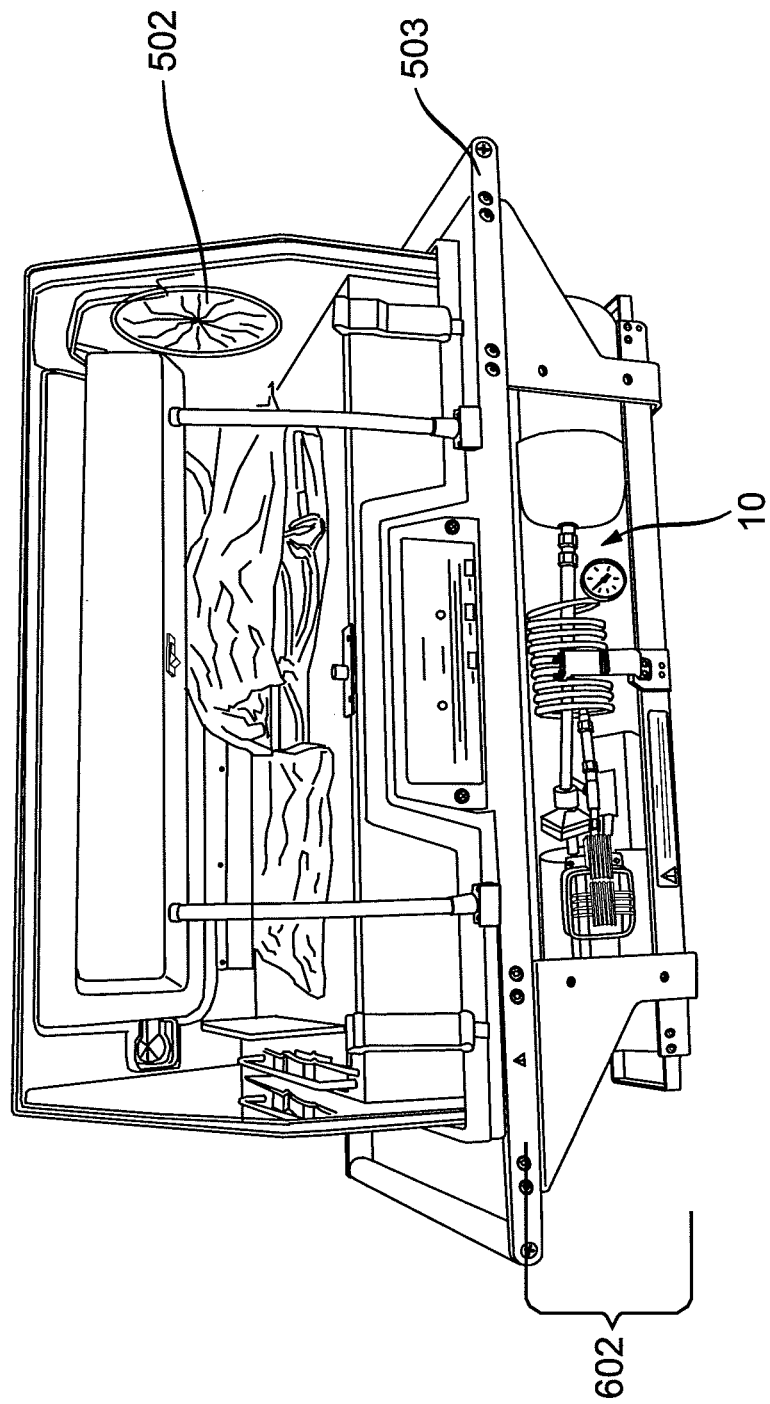
FIG. 6 is a side view showing exemplary usage of the apparatus according to invention principles.

FIG. 6 is a side view opposite the shown in FIG. 5. As can be seen herein, the incubator 502 includes a second cylinder storage region 602 enabling the incubator to be fit with two medical gas cylinders to provide medical grade air to a patient within the incubator 502. Similarly to the first cylinder storage region 504 in FIG. 5, the second cylinder storage region 602 is positioned on the underside of the platform 503 and has dimensions sufficient to receive a medical gas cylinder therein. As shown in FIG. 6, the apparatus 10 may also received within the second cylinder storage region 602 to provide a substantially continuous supply of medical grade air to a neonatal patient in the incubator 502 as needed.

Figure 7:
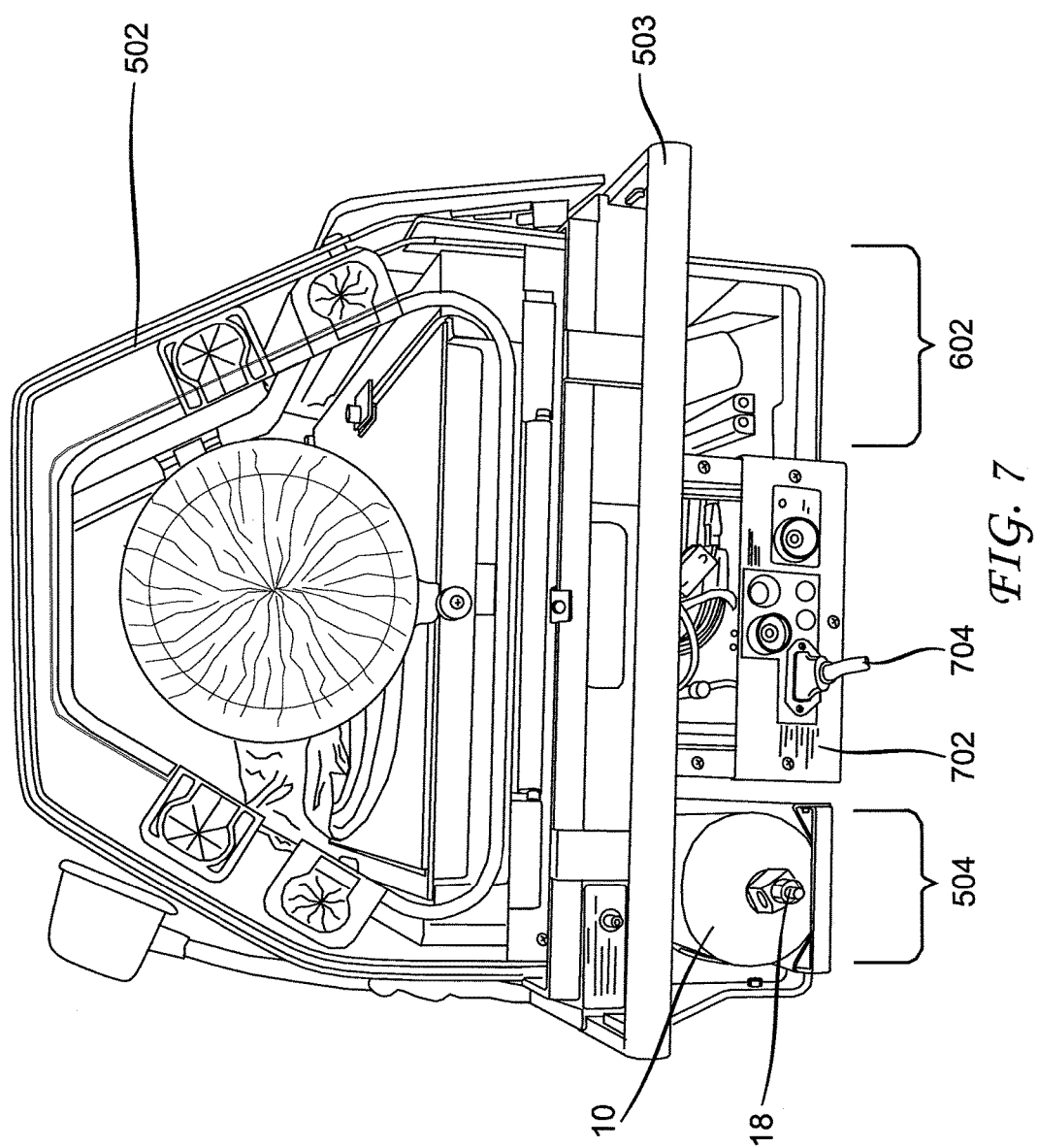
FIG. 7 is a front view showing an exemplary usage of the apparatus according to invention principles.

FIG. 7 is a front side view of the incubator 502 mounted on platform 503. As shown herein both the first cylinder storage region 504 and second cylinder storage region 602 is shown. However, only a single apparatus 10 is shown within the first cylinder storage region. The apparatus is oriented in this manner to ensure that the valve of the apparatus is proximate to the head of a patient in the incubator 502 to prevent any unintended tangling of tubes that are used (but not shown) to provide medical grade air to the patient in the incubator 502. Also shown herein is a power panel 702 that provides power to the apparatus 10 via a cord 704. This ensures that the apparatus is fully operational and may continuously use the ambient air to both provide a source of medical grade air to the patient and ensure proper operation of the medical air compressor components contained in the housing of the apparatus.

Figure 8:
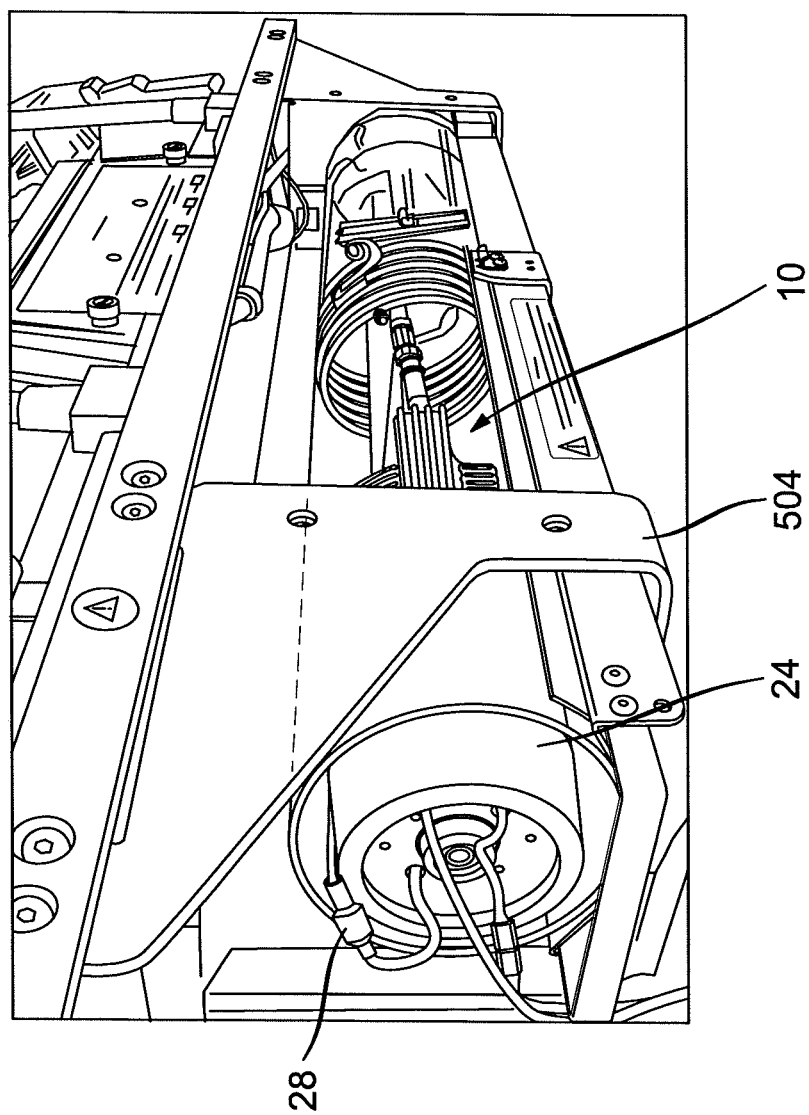
FIG. 8 is a rear perspective view showing an exemplary usage of the apparatus according to invention principles.

FIG. 8 is a rear perspective view of the first cylinder storage region 504 shown in FIG. 7. The apparatus 10 is shown retained within the first cylinder storage region 504. Also shown are the points at which the power connector 28 (FIG. 1A) connects the power panel 702 of FIG. 7 with the inner components of the apparatus 10. The wires connecting the power panel 702 with the second side 24 of the apparatus 10 are not shown and are preferably wired to prevent tangling with any other components of the incubator 502.

In this exemplary use of the apparatus 10, there are two regions where the apparatus 10 may be used. This configuration was previously important because conventional medical gas cylinders have a finite amount of gas therein. However, the apparatus 10 advantageously reduces the hardware required for use with the incubator 502 because a single apparatus provides the continuous source of medical grade air for the patient in the incubator as needed. Thus, by employing the apparatus 10 in a healthcare environment, certain devices may be redesigned or re-purposed to include additional medical devices that were unable to be used due directly to the need to keep two medical gas cylinders on hand during transport of the patient.

While FIGS. 5-8 describe an exemplary use of the apparatus, one skilled in the art would recognize that any medical device or apparatus that has been designed to carry, use or otherwise employ a conventional medical gas cylinder may use the apparatus 10. In another embodiment, the apparatus may be retained within a housing in an ambulance or a helicopter such that emergency responders will have a convenient and continuous source of medical grade air when responding to emergency situations. In another embodiment, patients afflicted with lung diseases such as emphysema who require an external supply of oxygen may employ the apparatus using the same transport cart currently used with a medical air cylinder. Thus, the apparatus reduces the need to refill and replace conventional medical air cylinders. In this embodiment, the apparatus would be powered by a rechargeable battery pack providing these patients with complete mobility along with the continuous supply of medical grade air.

In another embodiment, the apparatus shown in FIGS. 1A-4 may be used in a harness able to be strapped directly to a person in order to modify a pressure the ambient air. For example, the apparatus may be used to provide normally pressurized air at a higher altitude thereby improving the ability of the person to breathe at higher altitudes. The principle operation is as described above and the apparatus need only to be modified to change the pressure of the air provided to the user via the valve. In a further embodiment, the apparatus may also be connected and used with a pneumatic compression device thus enabling a patient to be ambulatory and still receive pneumatic compression therapy. The apparatus may supply a continuous source of air to the pneumatic compression device to inflate the cuffs as necessary. In another embodiment, the apparatus may be connected and used as part of a nebulizer as well as with pneumatic surgical and/or dental tools.

It will be understood that each of the elements described above, or two or more together may also find a useful application in other types of devices differing from the type described above.

While certain novel features have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit and scope of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

I claim:

1. An apparatus that provides a continuous source of medical grade air comprising:
   a substantially tubular and rigid housing including
      a first end;
      at least one aperture extending through the housing and positioned a predetermined distance from the first end;
      a second end, opposite the first end; and
      a tubular section between said first end and said second end;
   a valve extending from the first end of the housing for dispensing medical grade air to a patient;
   a medical grade air compressor that provides medical grade air for output by the valve, the medical grade air compressor being positioned within the housing on a side of the at least one aperture opposite the valve;
   an air flow generator positioned between the second end of the housing and the medical grade air compressor, the air flow generator draws air into the housing through the at least one aperture, the air passing over and around the medical grade air compressor to reduce a temperature of the medical grade air compressor and to the medical grade air compressor for generating medical grade air; and
   a reservoir fluidly coupled between said medical grade air compressor and said valve for receiving the medical grade air generated by the compressor, storing the medical grade air received from the compressor and providing the medical grade air received from the compressor to the valve for dispensing to the patient,
   wherein the at least one aperture includes a plurality of apertures positioned around a circumference of the housing.

2. The apparatus as recited in claim 1, wherein
   the air flow generator is at least one of (a) a fan; (b) a pump; and (c) a vacuum.

3. An apparatus that provides a continuous source of medical grade air comprising:
   a substantially tubular and rigid housing including
      a first end;
      at least one aperture extending through the housing and positioned a predetermined distance from the first end;
      a second end, opposite the first end; and
      a tubular section between said first end and said second end;
   a valve extending from the first end of the housing for dispensing medical grade air to a patient;
   a medical grade air compressor that provides medical grade air for output by the valve, the medical grade air compressor being positioned within the housing on a side of the at least one aperture opposite the valve;
   an air flow generator positioned between the second end of the housing and the medical grade air compressor, the air flow generator draws air into the housing through the at least one aperture, the air passing over and around the medical grade air compressor to reduce a temperature of the medical grade air compressor and to the medical grade air compressor for generating medical grade air; and
   a reservoir fluidly coupled between said medical grade air compressor and said valve for receiving the medical grade air generated by the compressor, storing the medical grade air received from the compressor and providing the medical grade air received from the compressor to the valve for dispensing to the patient,
   wherein the medical grade air compressor includes
      an air compressor that compresses air to a predetermined pressure;
      a first filter connected at an input of the air compressor, the first filter filters ambient particles having a size greater than a threshold size from the air;
      a second filter coupled to an output of the air compressor that filters oil and water and removes moisture from the compressed air; and
      a cooler assembly coupled to the second filter that receives the compressed air therethrough and dissipates heat from the compressed air.

4. The apparatus as recited in claim 3, wherein the cooler assembly includes a plurality of copper coils and the air drawn into the housing flows over and around the plurality of copper coils.

5. The apparatus as recited in claim 3, further comprising
   at least one of (a) a medical gas conditioning system; (b) a carbon dioxide filter and (c) a carbon monoxide detector.

6. An apparatus that provides a continuous source of medical grade air comprising:
   a substantially tubular and rigid housing including
      a first end;
      at least one aperture extending through the housing and positioned a predetermined distance from the first end;
      a second end, opposite the first end; and
      a tubular section between said first end and said second end;
   a valve extending from the first end of the housing for dispensing medical grade air to a patient;
   a medical grade air compressor that provides medical grade air for output by the valve, the medical grade air compressor being positioned within the housing on a side of the at least one aperture opposite the valve;
   an air flow generator positioned between the second end of the housing and the medical grade air compressor, the air flow generator draws air into the housing through the at least one aperture, the air passing over and around the medical grade air compressor to reduce a temperature of the medical grade air compressor and to the medical grade air compressor for generating medical grade air; and a reservoir fluidly coupled between said medical grade air compressor and said valve for receiving the medical grade air generated by the compressor, storing the medical grade air received from the compressor and providing the medical grade air received from the compressor to the valve for dispensing to the patient, further comprising at least one of a thermistor, a temperature sensor and a thermocouple coupled to the medical grade air compressor and the air flow generator, the at least one of thermistor, temperature sensor and thermocouple moveable between a first closed position and a second open position in response in detecting that a temperature of the medical grade air compressor has reached a threshold value.

7. An apparatus that provides a continuous source of medical grade air comprising:

a substantially tubular and rigid housing including
 a first end;
 at least one aperture extending through the housing and positioned a predetermined distance from the first end;
 a second end, opposite the first end; and
 a tubular section between said first end and said second end;
a valve extending from the first end of the housing for dispensing medical grade air to a patient;
a medical grade air compressor that provides medical grade air for output by the valve, the medical grade air compressor being positioned within the housing on a side of the at least one aperture opposite the valve;
an air flow generator positioned between the second end of the housing and the medical grade air compressor, the air flow generator draws air into the housing through the at least one aperture, the air passing over and around the medical grade air compressor to reduce a temperature of the medical grade air compressor and to the medical grade air compressor for generating medical grade air; and
a reservoir fluidly coupled between said medical grade air compressor and said valve for receiving the medical grade air generated by the compressor, storing the medical grade air received from the compressor and providing the medical grade air received from the compressor to the valve for dispensing to the patient, further comprising
one of a temperature sensor and a thermocouple coupled to the medical grade air compressor and the air flow generator, the one of a temperature sensor and a thermocouple moveable between a first closed position and a second open position in response to detecting that a temperature of the medical grade air compressor has reached a threshold value.

\* \* \* \* \*